United States Patent [19]

Grieshaber

[11] Patent Number: 4,752,983

[45] Date of Patent: Jun. 28, 1988

[54] SURGICAL INSTRUMENT CLEANING DEVICE

[76] Inventor: Herman R. Grieshaber, 2044 Balmoral La., Glenview, Ill. 60025

[21] Appl. No.: 71,416

[22] Filed: Jul. 9, 1987

[51] Int. Cl.⁴ .............................................. B24B 3/54
[52] U.S. Cl. .................................. 15/160; 15/210 B; 15/218.1
[58] Field of Search .............. 15/21 B, 210 R, 210 B, 15/218, 218.1, 160

[56] References Cited

U.S. PATENT DOCUMENTS

| | | | |
|---|---|---|---|
| 177,394 | 5/1876 | Hall et al. | 15/218.1 |
| 885,497 | 4/1908 | Maibaum | 15/39 |
| 1,732,467 | 4/1926 | Gregory | 15/423 |
| 1,901,262 | 3/1933 | Robideau | 15/104 R X |
| 2,121,307 | 6/1938 | Swift | 15/39 X |
| 2,202,516 | 5/1940 | Calleo | 15/104.5 X |
| 2,439,171 | 4/1948 | Kreider | 15/210 B |
| 2,659,922 | 11/1953 | Klein | 15/218 X |
| 2,744,276 | 5/1956 | Chambless | 15/104.92 |
| 2,810,923 | 10/1957 | Desso | 15/210 B |
| 2,898,620 | 8/1959 | Dickinson | 15/160 |
| 3,428,988 | 2/1969 | Blackburn | 15/160 |
| 3,583,018 | 6/1971 | Fink | 15/104.92 |
| 3,761,984 | 10/1973 | Hauschild et al. | 15/39 X |
| 3,982,357 | 9/1976 | Eldridge et al. | 15/218.1 X |
| 4,023,231 | 5/1977 | Haber | 15/210 B |
| 4,087,878 | 5/1978 | Grieshaber et al. | 15/218.1 X |
| 4,245,367 | 1/1981 | Stoute | 15/218.1 X |
| 4,380,839 | 4/1983 | Caradonna | 15/160 X |
| 4,419,781 | 12/1983 | Meegan | 15/210 B |
| 4,446,967 | 5/1984 | Halkyard | 206/368 |
| 4,506,404 | 3/1985 | Clay | 15/244 C |

FOREIGN PATENT DOCUMENTS

| | | | |
|---|---|---|---|
| 2702242 | 8/1977 | Fed. Rep. of Germany . | |
| 975351 | 10/1950 | France | 15/39 |
| 57351 | 8/1946 | Netherlands | 15/104.92 |
| 338327 | 6/1959 | Switzerland | 15/210 B |
| 290641 | 8/1928 | United Kingdom | 15/39 |

Primary Examiner—Chris K. Moore
Attorney, Agent, or Firm—Neuman, Williams Anderson & Olson

[57] ABSTRACT

A device is provided which is adapted for use in surface cleaning a soiled portion of a surgical instrument. The device includes a hollow casing having an elongated slot formed in an exterior surface of the casing. The slot permits the soiled portion of the surgical instrument to be inserted into the casing interior and be moved longitudinally of the slot. A friction medium is disposed within the hollow casing and has a segment thereof aligned with the slot. The aligned segment is adapted to exert frictional force on the inserted surgical instrument portion and effect surface cleaning thereof when the instrument is moved longitudinally of the slot. The device also includes an elongated directing element which is adapted to selectively assume a first or second mode. When in the first mode, the element is exposed and aligned with the slot and is engaged by the inserted instrument portion. The engaged element controls the lateral motion of the inserted instrument portion as the latter moves longitudinally of the slot. When in the second mode, the directing element is concealed within the casing and is not accessible for engagement by the inserted instrument portion.

15 Claims, 1 Drawing Sheet

SURGICAL INSTRUMENT CLEANING DEVICE

BACKGROUND OF THE INVENTION

When surgical instruments such as cautery forceps, knifes, scalpels, and the like are used in performing surgery, they often become soiled with particles of tissue, blood, or other matter. These materials can become firmly adhered to the instrument and severely hinder their further use. This is a particular problem with multiple member instruments such as cautery forceps which require close contact between the tissue to be treated and the two or more operative surfaces of the instrument.

In addition, any blood or tissue dried onto segments of the instruments after surgery can be extremely difficult to remove and may prevent the proper sterilization of the instruments. When multiple member instruments such as cautery forceps must be cleaned, there is often the further difficulty of cleaning the interior surfaces of the instruments that may be difficult to reach effectively.

These problems have frequently been avoided by immediately wiping the instruments with disposable gauze or other cleaning materials during surgery as the need arises. This procedure, however, requires that the surgeon or his assistant interrupt the surgery to clean the instruments, using both hands and taking great care to avoid accidental cuts or injuries or to avoid damaging the surgical instruments. This cleaning procedure is not only very disruptive to the surgery, but also requires a significant supply of readily accessible gauze sheets and a convenient place to dispose of the soiled gauze.

Attempts to provide cleaning devices for surgical instruments include the device disclosed in U.S. Pat. No. 4,087,878, which requires the surgeon to insert his instrument into a casing through a slot to brush the instrument against setae members and then scrape the instrument against the reinforced edges of the slot as the instrument is withdrawn. This device requires many different parts including a base, a hollow casing, and a means for reinforcing the slot.

The surgeon, in addition, must ensure that such a device is correctly aligned and that the soiled portion of the instrument is carefully inserted through the proper part of the slot so that the instrument is both brushed and scraped to obtain a complete cleaning action. Finally, such devices, at times, must be used repeatedly to consistently and completely clean the soiled instruments of all adhering tissue and blood.

Other cleaning devices are unsuitable for use with surgical instruments as they often would damage or dull the sharp edges of the instruments or would not adequately clean the instruments without a substantial disruption of the surgery. In addition, these devices do not actually address or teach a solution to the problem of cleaning multiple member surgical instruments such as cautery forceps. These devices also require the assembly of many different elements, including rollers and the like, before they may be put into practice. The prior art cleaners are generally limited to a single cleaning task and are not alterable to clean, for example, cautery blades as well as cautery forceps.

OBJECTS OF THE INVENTION

The object of the invention is to provide a simple and inexpensive device that will more efficiently and effectively remove particles of tissue, blood and the like from surgical instruments, in particular cautery forceps. This is done without the use of numerous parts or special reinforcing elements that must be consciously utilized by the surgeon to obtain the maximum cleaning action. The invention also does not require the careful placement of the surgical instrument into a particular portion of the slot formed on the device, and each use cleans the instrument more completely than is possible with the prior devices.

It is a further object of the invention to provide a surgical instrument cleaning device that is compact and sturdy, and can be easily positioned during surgery without interfering with the activities of the surgeon or assisting personnel.

It is a still further object of the invention to provide a single surgical instrument cleaning device that may be used repeatedly during surgery and then may be easily discarded.

It is a still further object of the invention to provide a surgical instrument cleaning device that may be used without significantly disrupting the surgical procedure.

It is a still further object of the invention to provide a surgical instrument cleaning device that allows the user to clean surgical instruments without contacting the soiled portion of the instrument with his or her hands.

It is still a further object of the invention to provide a surgical instrument cleaning device that will accommodate a variety of types and sizes of surgical instruments.

It is still a further object of the invention to provide a surgical instrument cleaning device that is convertible to be usable for multiple cleaning tasks.

Further and additional objects will appear from the description, accompanying drawings, and appended claims.

SUMMARY OF THE INVENTION

One embodiment of the improved device for cleaning a soiled segment of a surgical instrument, such as cautery forceps, includes a hollow casing having a base portion and upwardly extending wall portions that form an elongated slot in an exterior surface of the casing. The slot is arranged so that the soiled portion of a surgical instrument may be inserted through the slot into the casing and may be moved longitudinally of the slot. A frictional medium is disposed within the hollow casing and is adapted to exert frictional force on the inserted surgical instrument segments to effect cleaning thereof when the instrument is moved longitudinally of the slot. The device is further provided with a directing means that urges the soiled portion of the instrument back and forth, in opposing directions transverse of the slot when the instrument is moved longitudinally thereof.

DESCRIPTION

For a more complete understanding of the invention, reference should be made to the drawings wherein.

Figure 1:
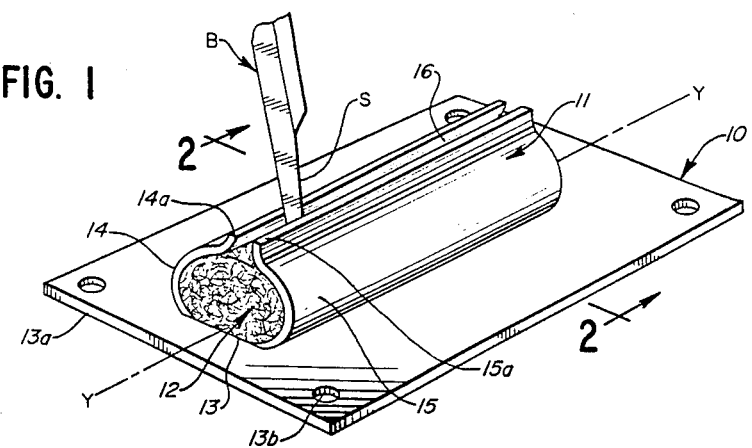
FIG. 1 is a perspective end view of one form of the surgical instrument cleaning device shown in one mode for cleaning the soiled end segments of cautery forceps.

Referring now to the drawings and more particularly to FIG. 1, a preferred embodiment of the surgical instrument cleaning device 10 is shown in a first mode I for use in cleaning the soiled segments S and S' of a surgical instrument F, e.g., cautery forceps.

During surgery, a surgical instrument, such as cautery forceps, often becomes soiled with particles of tissue, blood, or other matter. It is necessary during the surgery to repeatedly clean the instrument of this material as soon a possible so as to allow further unhindered use of the instrument and to allow the instrument to be properly sterilized after surgery has been concluded.

Figure 2:
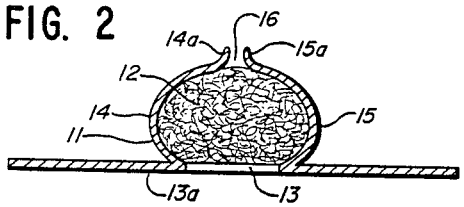
FIG. 2 is a perspective exploded view of the device of FIG. 1.
Figure 3:
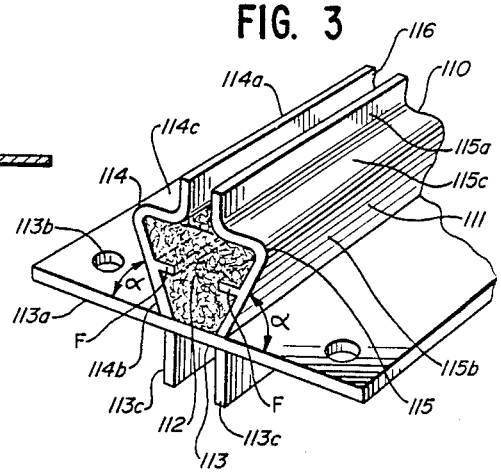
FIG. 3 is an end view of the device of FIG. 1.

The device 10 as shown in FIGS. 1, 2 and 3 includes an elongated casing 12, a frictional medium 14 disposed within the casing 10, and a directing means 16. The casing 10 is preferably extruded from a rigid aluminum material or an inexpensive, semi-rigid, plastic material (e.g. Melamine resin) and includes a base portion 18 and upwardly extending wall portions 20 and 22. The casing 12 may also be open at each end as depicted in the figures, or the ends of the casing may be closed and sealed. Another embodiment of the casing 12 has only one end closed and sealed.

The wall portions 20 and 22 coact to form a narrow, elongated slot 24 on the upper exterior of the casing 12. The slot is disposed in a substantially parallel relation with the longitudinal axis Y—Y of the casing 12. The edges 26a of the wall portions defining the slot 24 are usually disposed in a spaced, substantially parallel relation. If desired, however, the edges may converge towards one end of the slot so as to accommodate different size instruments.

The upwardly extending wall portions 20 and 22 of the casing 10 are also preferably formed so that they curve inwardly to give the casing 10 a generally cylindrical cross-section as can be seen in FIGS. 1-3. The edges 26a of the wall portions adjacent slot 24 are also preferably formed as upwardly extending flanges, as shown in the drawings and act to aid the user's placement and longitudinal movement of the soiled segments S and S' of the instrument F within the slot 24 to ensure a complete cleaning action.

The frictional medium 14 is mounted within casing 12 and extends at least the full length of the slot 24. The frictional medium 14 may be fixed within the casing 12 or may be slidably mounted within the casing 12 so that it is removable through an open end of the casing. The frictional medium is preferably a setose member 28, as shown in FIG. 2, having a core 30 and setae 32 fixed thereto. The setae 32 extend radially outwardly from the core 30, along substantially the entire length of the core, and are disposed with their axes substantially normal to the core 30.

The frictional medium 14 may also be comprised of dense wire clusters, an abrasive like sponge or other similar frictional materials. When a frictional medium composed of these types of materials is disposed within the casing 12, the frictional medium 14 may be in a compressed state because either the medium is compressed prior to its disposition within the casing 12 and is retained in its compressed state by the casing wall portions 20 and 22, or because the casing walls are resilient and exert an inward compressive force against the medium after its disposition therein.

The directing means 16, as shown in FIG. 2, includes an elongated bail member 34 having two depending end support segments 34a. Each side edge of the bail member has an undulating configuration forming a series of arcuate segments 34b, 34c, and 34d. The arcuate segments 34b, 34c and 34d extend in opposite directions relative to the slot 24. The bail member is preferably composed of a metallic material such as surgical stainless steel, but may also be composed of a synthetic plastic like that of the casing 12 or other such materials.

The support segments 34a are provided with openings 36 that accommodate the ends of core member 30 thereby fixing the bail member 34 relative to the setose medium 28. When the combination of the bail member 34 and setose frictional medium 28 is inserted into the casing 12, said bail member 34 is disposed in a position approximately equidistant from the wall portion edges 26a. If alternative frictional media are used, such as the compressed sponge material discussed above, then the support segments 34a may be fixed to suitable securing means integrated with the frictional medium 14 or to brackets, not shown, formed on the base portion 18 of the device. The invention is not, however, limited to any particular securing means.

The preferred embodiment of the invention is also provided with inwardly directed protuberances 38 formed on wall portions 20 and 22 and longitudinally of the casing 12. The protuberances 38 retain and resist relative rotation of the frictional medium 14 within the casing interior. Other protuberance configurations or means may be used for retaining the frictional medium within the casing interior. Other configurations of protuberances may also be used, as well as other types of means for securing the frictional medium 14 within the casing.

The base portion 18 of the casing 10 is preferably of a planar configuration and has marginal portions 18a extending laterally outward a substantial distance beyond the wall portions 20 and 22. The size of the base portion 18 relative to the entire casing 10 provides stability to the device when it is resting on a table top or other suitable surface. Apertures may also be provided at the corners of the marginal portion to allow clamping or pinning of the device to a solid or fabric surface.

From the above description, it can be seen that the soiled segments S and S' of instrument F are cleaned by inserting the soiled segments so as to straddle the directing means 16, and then moving the segments longitudinally of slot 24 and directing means 16. The frictional medium 14 will thereby engage the surfaces of the soiled segments S and S' and exert frictional force thereagainst so as to effect cleaning thereof. At the same time, and with the same longitudinal motion of the segments, the directing means 16 will urge the segments to swerve within the slot thereby maximizing frictional contact between the soiled segments and the medium 14 with efficiency and economy of effort.

The cleaning action of the device thus ensures a consistent and complete stripping or scraping of tissue or blood particles from the soiled segments' surfaces without dulling or damaging the instrument F. This cleaning action is obtained without the need for the surgeon or assistant to contact directly or wipe the soiled segments of the instrument F with gauze or the like. Accordingly, the resulting possibility of injury to the user or damage to the instrument is greatly reduced.

While the soiled segments S and S' of instrument F are normally inserted into one end of slot 24 (the wide end where the edges converge) and moved longitudinally thereof to the other end, such a procedure is not necessary in all situations. For example, where the soiled condition of the instrument segments is less severe, the segments may be inserted into or removed from the slot at any point. Longitudinal movement of the soiled segments S and S' in either direction along the slot will result in optimum cleaning of the instrument.

Figure 4:
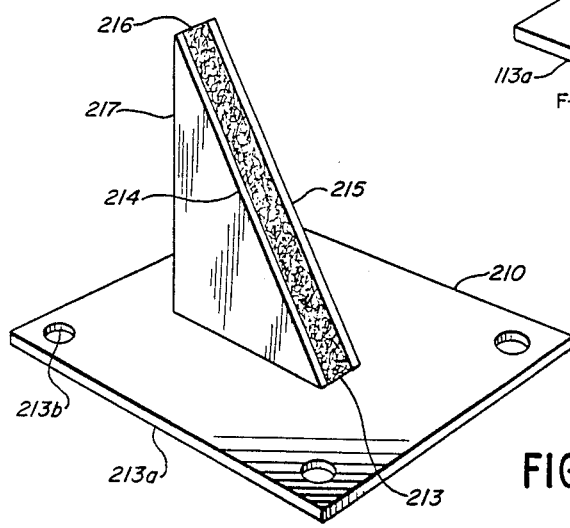
FIG. 4 is a perspective end view of the device in a second mode for cleaning a single bladed surgical instrument.

When device 10 is in a second mode II, as shown in FIG. 4, the directing means 16 is not exposed within slot 24. To change from mode I to mode II merely requires endwise removal of the frictional medium 14 from the casing 12 through an access opening A and then rotating the medium about its longitudinal axis a sufficient amount so that when the medium is reassembled within the casing the directing means 16 is out of registry with the slot 24. Thus, only the setae 32 of member 28 are exposed in the slot 24 when the device is in mode II. When in mode II, the device is particularly suitable for cleaning instruments having a single blade or tongue.

This is a particular advantage when it is desirable to purchase a single version of the invention for use with surgical instruments with multiple soiled portions such as cautery forceps and instruments with unitary soiled portions such as cautery blades or scalpels.

Thus, it will be seen that a simple and inexpensive surgical instrument cleaning device has been provided which is readily capable of effectively and expeditiously cleaning a wide variety of surgical instruments. The improved device does not require elaborate and time-consuming procedures in order to properly clean the soiled instrument.

The device is of compact and sturdy construction. It can be conveniently positioned during surgery and may be used repeatedly without disrupting the surgical procedure. Furthermore, the device eliminates the need for the soiled portion of the instrument to be in direct contact with the hand or fingers of the surgeon or assistant when the instrument is being cleaned. The shape and size of the improved device may vary from that shown without departing from the scope of the invention.

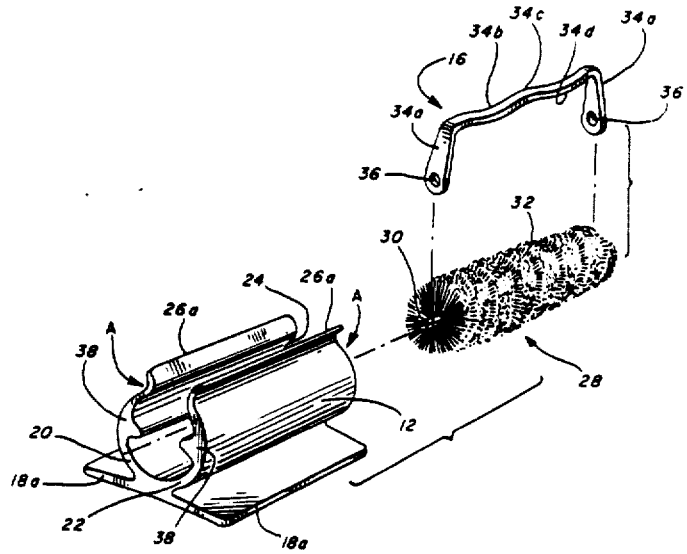

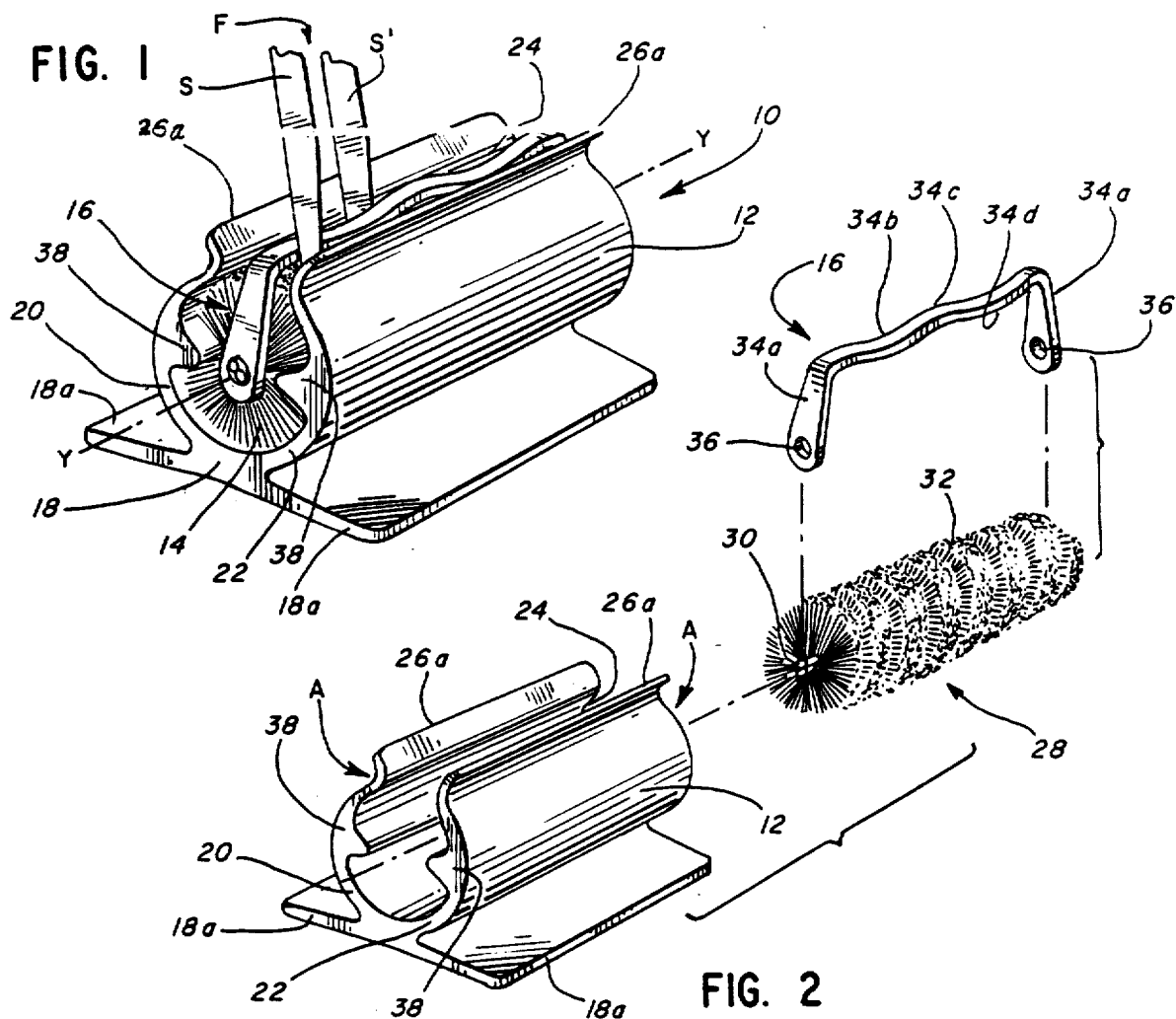
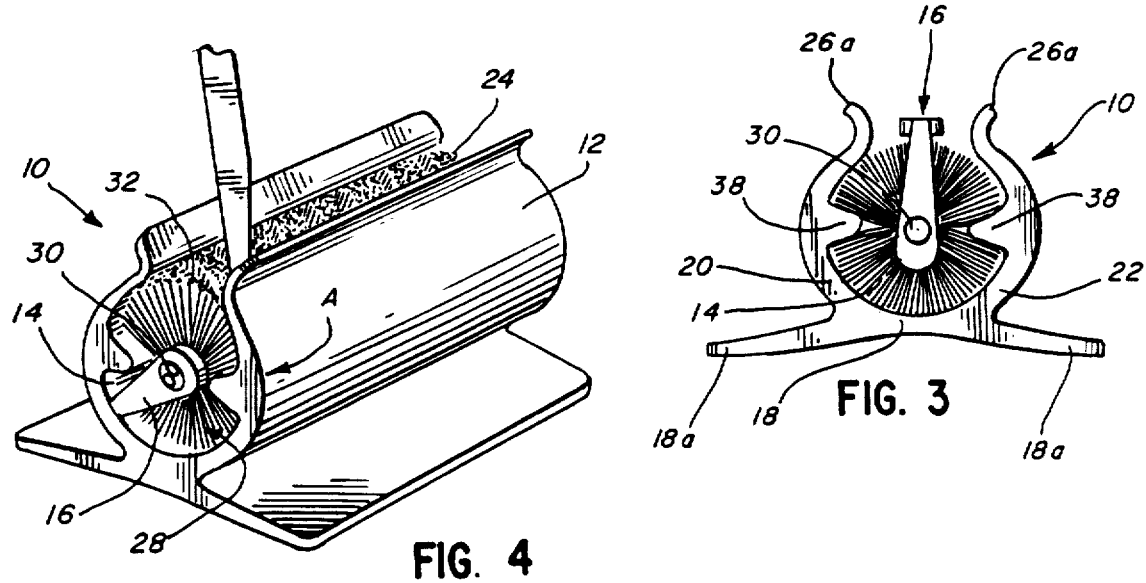

I claim:

1. A device for surface cleaning a soiled portion of a surgical instrument, comprising a hollow casing having an exposed surface provided with an elongated slot sized to accommodate and guide the soiled instrument portion when the latter is inserted through the slot and moved longitudinally thereof; directing means adapted to be exposed within said slot and extending longitudinally thereof for engagement by the inserted instrument portion and controlling lateral motion thereof as the inserted portion is moved longitudinally of the slot; friction means disposed within said casing and having a portion thereof aligned with said slot and in close proximity to said directing means, said aligned friction means adapted to be engaged by the inserted soiled instrument portion and effect surface cleaning thereof as the portion is moved longitudinally thereof; and means for retaining said directing means and friction means in predetermined relative positions within said casing.

2. The device of claim 1 wherein the portion of the directing means engaged by the inserted instrument portion has a configuration whereby a swerving motion is imparted to the inserted instrument portion as the latter is moved longitudinally of the slot.

3. The device of claim 2 wherein the directing means is adapted to be straddled by the inserted instrument portion.

4. The device of claim 2 wherein the exposed surface of the casing is provided with upwardly extending guide means defining elongated peripheral segments of the slot.

5. The device of claim 1 wherein the directing means includes an elongated bail member having a segment of said bail member adapted to be slidably engaged by the inserted instrument portion and having an undulating configuration.

6. The device of claim 1 wherein the frictional means includes an elongated setose member with a central core having elongated resilient setae substantially fixed thereto and extending substantially radially therefrom.

7. The device of claim 6 wherein the directing means includes a bail member having depending support segments engaging opposite ends of the central core of the setose member.

8. The device of claim 1 wherein the frictional means and the directing means are removable as unit from the hollow casing through an access opening formed in said casing; upon reassembling the frictional means and the directing means as a unit within the casing through the access opening, the directing means may assume either a first or second mode; when in the first mode, said directing means is aligned with the casing slot, and when in the second mode, said directing means is in nonregistered relation with said slot.

9. The device of claim 1 wherein the means for retaining said directing means and friction means in predetermined relative positions within the casing includes protuberances frictionally engaging a concealed perimetric segment of the friction means.

10. A device for use in surface cleaning portions of surgical instruments, such as cautery forceps, soiled with adherent liquid and non-liquid matter, comprising a hollow casing having an exposed surface provided with an elongated narrow slot sized to accommodate and guide the soiled instrument portions when the latter are inserted through the slot and moved longitudinally thereof; directing means extending longitudinally of said slot for controlling lateral motion of the inserted portions when the latter are moved longitudinally thereof; and friction means disposed within said casing and having an elongated portion thereof aligned with said slot and being accessible to the instrument portions through said slot, said friction means being in resilient engagement with segments of the casing circumjacent the slot and being adapted to exert a compressive frictional force on the inserted soiled instrument portions to effect surface cleaning thereof when the soiled instrument portions are moved longitudinally of said slot.

11. The device of claim 10 wherein the hollow casing has an interior of a generally cylindrical cross-sectional configuration, and the exterior of said casing is provided with upwardly extending guide means defining elongated sides of the slot.

12. The device of claim 10 wherein the directing means includes a bail member having elongated surfaces adapted to be engaged by the inserted instrument portions, said surfaces having an undulating configuration.

13. The device of claim 12 wherein the bail member and friction means are removable as a unit from the hollow casing through an access opening formed therein; the bail member and friction means are reassembled as a unit with the casing through the access opening whereby the bail member may assume either a first or second mode; when in the first mode the bail member is exposed and aligned with said slot and when in the second mode is concealed and in non-registered relation with said slot.

14. The device of claim 10 wherein the friction means is formed of a synthetic or natural, resilient coarse material.

15. The device of claim 10 wherein the hollow casing interior is provided with an inwardly extending protuberance, retaining the friction means and the bail member in a selected mode.

* * * * *

UNITED STATES PATENT AND TRADEMARK OFFICE
CERTIFICATE OF CORRECTION

PATENT NO. : 4,752,983

DATED : June 28, 1988

INVENTOR(S) : Herman R. Grieshaber

It is certified that error appears in the above-identified patent and that said Letters Patent is hereby corrected as shown below:

The title page should be deleted to appear as per attached title page.

Figures 1-4 should be deleted to be replaced with figures 1-4 as shown on the attached sheet.

Signed and Sealed this

Second Day of May, 1989

Attest:

DONALD J. QUIGG

Attesting Officer

Commissioner of Patents and Trademarks

United States Patent [19]

Grieshaber

[11] Patent Number: 4,752,983
[45] Date of Patent: Jun. 28, 1988

[54] SURGICAL INSTRUMENT CLEANING DEVICE

[76] Inventor: Herman R. Grieshaber, 2044 Balmoral La., Glenview, Ill. 60025

[21] Appl. No.: 71,416

[22] Filed: Jul. 9, 1987

[51] Int. Cl.⁴ .................................. B24B 3/54
[52] U.S. Cl. ........................ 15/160; 15/210 B; 15/218.1
[58] Field of Search ........... 15/21 B, 210 R, 210 B, 15/218, 218.1, 160

[56] References Cited

U.S. PATENT DOCUMENTS

| | | | |
|---|---|---|---|
| 177,394 | 5/1876 | Hall et al. | 15/218.1 |
| 885,497 | 4/1908 | Maibaum | 15/39 |
| 1,732,467 | 4/1926 | Gregory | 15/423 |
| 1,901,262 | 3/1933 | Robideau | 15/104 R X |
| 2,121,307 | 6/1938 | Swift | 15/39 X |
| 2,202,516 | 5/1940 | Calleo | 15/104.5 X |
| 2,439,171 | 4/1948 | Kreider | 15/210 B |
| 2,659,922 | 11/1953 | Klein | 15/218 X |
| 2,744,276 | 5/1956 | Chambless | 15/104.92 |
| 2,810,923 | 10/1957 | Desso | 15/210 B |
| 2,898,620 | 8/1959 | Dickinson | 15/160 |
| 3,428,988 | 2/1969 | Blackburn | 15/160 |
| 3,583,018 | 6/1971 | Fink | 15/104.92 |
| 3,761,984 | 10/1973 | Hauschild et al. | 15/39 X |
| 3,982,357 | 9/1976 | Eldridge et al. | 15/218.1 X |
| 4,023,231 | 5/1977 | Haber | 15/210 B |
| 4,087,878 | 5/1978 | Grieshaber et al. | 15/218.1 X |
| 4,245,367 | 1/1981 | Stoute | 15/218.1 X |
| 4,380,839 | 4/1983 | Caradonna | 15/160 X |
| 4,419,781 | 12/1983 | Meegan | 15/210 B |
| 4,446,967 | 5/1984 | Halkyard | 206/368 |
| 4,506,404 | 3/1985 | Clay | 15/244 C |

FOREIGN PATENT DOCUMENTS

| | | | |
|---|---|---|---|
| 2702242 | 8/1977 | Fed. Rep. of Germany | |
| 975351 | 10/1950 | France | 15/39 |
| 57351 | 8/1946 | Netherlands | 15/104.92 |
| 338327 | 6/1959 | Switzerland | 15/210 B |
| 290641 | 8/1928 | United Kingdom | 15/39 |

*Primary Examiner*—Chris K. Moore
*Attorney, Agent, or Firm*—Neuman, Williams Anderson & Olson

[57] ABSTRACT

A device is provided which is adapted for use in surface cleaning a soiled portion of a surgical instrument. The device includes a hollow casing having an elongated slot formed in an exterior surface of the casing. The slot permits the soiled portion of the surgical instrument to be inserted into the casing interior and be moved longitudinally of the slot. A friction medium is disposed within the hollow casing and has a segment thereof aligned with the slot. The aligned segment is adapted to exert frictional force on the inserted surgical instrument portion and effect surface cleaning thereof when the instrument is moved longitudinally of the slot. The device also includes an elongated directing element which is adapted to selectively assume a first or second mode. When in the first mode, the element is exposed and aligned with the slot and is engaged by the inserted instrument portion. The engaged element controls the lateral motion of the inserted instrument portion as the latter moves longitudinally of the slot. When in the second mode, the directing element is concealed within the casing and is not accessible for engagement by the inserted instrument portion.

15 Claims, 1 Drawing Sheet